(12) United States Patent
Peng (10) Patent No.: US 9,328,849 B2
(45) Date of Patent: May 3, 2016

(54) MICRODEVICE STRUCTURE OF MICROCHANNEL CHIP

(76) Inventor: Xingyue Peng, Xiamen (CN)

( * ) Notice: Subject to any disclaimer, the term of this patent is extended or adjusted under 35 U.S.C. 154(b) by 576 days.

(21) Appl. No.: 14/240,790

(22) PCT Filed: Sep. 14, 2010

(86) PCT No.: PCT/CN2010/076904
§ 371 (c)(1),
(2), (4) Date: Feb. 25, 2014

(87) PCT Pub. No.: WO2012/034270
PCT Pub. Date: Mar. 22, 2012

(65) Prior Publication Data
US 2015/0107709 A1 Apr. 23, 2015

(51) Int. Cl.
*F15C 1/06* (2006.01)
*F16K 99/00* (2006.01)
(Continued)

(52) U.S. Cl.
CPC ........... *F16K 99/0017* (2013.01); *B01L 3/5027* (2013.01); *B01L 3/50273* (2013.01); *B01L 3/502738* (2013.01); *B01L 3/502746* (2013.01); *F04B 9/12* (2013.01); *F04B 19/006* (2013.01); *F16K 99/0021* (2013.01); *F16K 99/0057* (2013.01); *G01N 13/02* (2013.01); *B01L 2200/0621* (2013.01); *B01L 2200/10* (2013.01); *B01L 2200/14* (2013.01); *B01L 2200/16* (2013.01); *B01L 2300/0816* (2013.01); *B01L 2300/0861* (2013.01); *B01L 2300/0887* (2013.01); *B01L 2400/0487* (2013.01);
(Continued)

(58) Field of Classification Search
CPC ................... F16K 99/0017; F16K 2099/0084; F16K 2099/0094; B91L 3/50273; B91L 3/502738; B91L 3/502746; B91L 3/5027; B91L 2200/0621; B91L 2200/10; B91L 2200/14; B91L 2200/16; B91L 2300/0816; B91L 2300/0861; B91L 2300/0887; B91L 2400/0487; B91L 2400/688; B91L 2400/082; F04B 9/12; F04B 19/006; G01N 13/02; G01N 35/1097; Y10T 137/2076; Y10T 137/218; Y10T 137/2224
USPC ..................... 137/825, 833; 422/502, 503, 70
See application file for complete search history.

(56) References Cited

U.S. PATENT DOCUMENTS

| | | | | |
|---|---|---|---|---|
| 4,676,274 A | * | 6/1987 | Brown | ................ B01L 3/50273 137/252 |
| 6,296,020 B1 | * | 10/2001 | McNeely | .............. B01F 5/0403 137/806 |

(Continued)

*Primary Examiner* — Craig Schneider
*Assistant Examiner* — Minh Le (57) ABSTRACT

A microdevice structure of microchannel chip is provided which includes one gas channel and at least one liquid channel. The microchannel connects the gas channel and each liquid channel. The most basic microdevice of the mirochannel chip comprises micropressure sensor, microvalve, micropiston and micropump which are controlled by digital pressure gas microcircuit in the chip. Each microdevice isolates the gas phase and liquid phase by microhole without any movable component and any special ventilate or elastic material. The gas-liquid interface is driven by the pressure difference of gas phase and liquid phase to enable the microdevice to implement the functions, such as sensing pressure, switching fluid channel, transporting liquid effectively, and so on. All kinds of microdevices can be shaped on the hard material (for example glass) by etching, so as to integrate a great lot microdevices with low cost, and the structure of chip and these several microdevices can be formed by adopting other methods on other material.

2 Claims, 12 Drawing Sheets

(51) Int. Cl.
*B01L 3/00* (2006.01)
*F04B 9/12* (2006.01)
*F04B 19/00* (2006.01)
*G01N 13/02* (2006.01)
*G01N 35/10* (2006.01)

(52) U.S. Cl.
CPC .... *B01L2400/0688* (2013.01); *B01L 2400/082* (2013.01); *F16K 2099/0084* (2013.01); *F16K 2099/0094* (2013.01); *G01N 35/1097* (2013.01); *Y10T 137/2076* (2015.04)

(56) References Cited

U.S. PATENT DOCUMENTS

| | | | | |
|---|---|---|---|---|
| 6,601,613 B2* | 8/2003 | McNeely | ............ | B01F 5/0403 137/806 |
| 7,134,453 B2* | 11/2006 | Peters | ............ | B01L 3/502738 137/806 |
| 7,412,990 B2* | 8/2008 | Chung | ............ | B01F 13/0086 137/807 |
| 8,133,456 B2* | 3/2012 | Higashino | ............ | B01J 19/0093 422/500 |
| 8,376,317 B2* | 2/2013 | Chuang | ............ | B01F 5/102 251/129.01 |
| 8,919,383 B2* | 12/2014 | Rodenfels | ............ | B01L 3/5027 137/829 |
| 2006/0289309 A1* | 12/2006 | Fukuzawa | ............ | B01J 19/0093 204/451 |
| 2007/0113908 A1* | 5/2007 | Lee | ............ | B01L 3/502738 137/833 |
| 2007/0207063 A1* | 9/2007 | Hsieh | ............ | B01L 3/502738 422/400 |
| 2010/0101660 A1* | 4/2010 | Kitamura | ............ | F16K 99/0001 137/109 |
| 2010/0234674 A1* | 9/2010 | Wheeler | ............ | F16K 99/0001 600/35 |
| 2013/0206250 A1* | 8/2013 | Zhang | ............ | B01L 3/502738 137/237 |
| 2015/0125947 A1* | 5/2015 | Korczyk | ............ | B01L 3/502738 435/289.1 |

* cited by examiner

MICRODEVICE STRUCTURE OF MICROCHANNEL CHIP

BACKGROUND OF THE INVENTION

1. Field of the Invention

The present invention relates to a microchannel chip manufacture, and more particularly to a microdevice structure of a microchannel chip.

2. Description of the Prior Art

These days, a chip laboratory (lab on a chip) is developed rapidly, which can be widely used to laboratory research and daily medical testing technology in different fields, such as life sciences, chemistry and physics. Microfluid chip technique is the main technique of the chip laboratory. Microfluid is the transportation carrier of the substance in the chip laboratory, such as various dissolving compound in the liquid phase, the cell of a culture medium, and so on. It is important to control the microchannel on the chip and the fluid in various chip microdevices to flow and transfer precisely so as to drive the normal work of the microfluid chip. Therefore, the basest and the most important parts in the microfluid chip are micro devices, namely, the pump of the microfluid on the chip (MISPU), the valve (switch), the static pressure sensor to sense the pressure of the microfluid, or the speed sensor to sense the velocity of the microfluid.

The manufacturing process of the existing microdevice, such as MISPU, MISVA, and the like, is complicated and doesn't have ideal performance. Although researchers in this field endeavor to overcome the shortcomings and invent new technologies, the technical defects of the existing microdevices, such as MISPU, MISVA, and the like, still limit the microfluid chip to be used widely. For example, the pump outside the chip (not inside the chip) is the main device to drive the fluid inside the chip. The existing microdevices use electric control, magnetic control, diaphram control and so on, for example, electroosmotic pump or electrokinetic gating valve. The direct effect of voltage cannot be applied to each fluid system, and it may interfere with the chemical and physical environments of the system. If the microdevice uses magnetic control, it can use ferrofluid. The movement of the ferrofluid is controlled by the movement of an external permanent magnet for opening and closing the valve and for operation of the pump. However, the ferrofluid itself will be in contact with the fluid system in the microchannel of the chip. The control of the external permanent magnet is complex and difficult to automate. The diaphragm control is still the most widely used way. By using a deformable material, such as PDMS (polydimethylsiloxane), the operation of the valve and the pump is controlled by applying a force on the diaphragm. The advantage of the diaphragm pump is durable, like a mechanical pump. However, it also has shortcomings. It is required to use a deformable material as the diaphragm. This cannot prevent the system from being polluted and interfered by the material. Besides, the diaphragm pump itself is complex, so the manufacture cost and its lifespan are not ideal.

Therefore, the key technique of the existing microfluid chip, such as MISPU, MISVA, has the foresaid shortcomings. In particular, for a glass chip (having the best optics quality and chemical quality), because glass is a non-deformable rigid material, the glass chip cannot be provided with a built-in pump/valve system, such that the further development of the glass chip is greatly limited.

Accordingly, the inventor of the present invention has devoted himself based on his many years of practical experiences to solve this problem.

SUMMARY OF THE INVENTION

The primary object of the present invention is to provide a microdevice structure of a microchannel chip. The microchannel controls the microdevice to be formed on a hard chip by etching.

In order to achieve the aforesaid object, the microdevice structure of the present invention includes a gas channel and at least one liquid channel. The gas channel communicates with the at least one liquid channel through a microchannel.

Preferably, the microdevice structure is a micro surface tension sensor. The micro surface tension sensor includes a gas channel and a liquid channel. One end of the gas channel is in communication with a gas. Another end of the gas channel communicates with one end of the liquid channel through a tapered microchannel. Another end of the liquid channel is in communication with a liquid.

Preferably, the microdevice structure is a micro surface tension valve. The micro surface tension valve includes a gas channel and at least two liquid channels. One end of the gas channel is in communication with a gas. Another end of the gas channel communicates with one end of one of the at least two liquid channels through a tapered microchannel. At least one side of the microchannel is in communication with one end of the other liquid channel through another tapered microchannel. Another end of each of the at least two liquid channels is in communication with a liquid.

Alternatively, the microdevice structure is a micro surface tension valve. The micro surface tension valve includes a gas channel and three liquid channels. One end of the gas channel is in communication with a gas. Another end of the gas channel communicates with one end of one of the three liquid channels through a tapered microchannel. Two sides of the microchannel are respectively in communication with one end of each of the other two liquid channels through another tapered microchannel. Another end of each of the three liquid channels is in communication with a liquid.

Preferably, the microdevice structure is a micro surface tension piston. The micro surface tension piston includes a gas channel and a liquid channel. One end of the gas channel is in communication with a gas. Another end of the gas channel communicates with a middle section of the liquid channel through a tapered microchannel. Two ends of the liquid channel are respectively in communication with a liquid.

Preferably, the microdevice structure is a micro surface tension pump composed of two micro surface tension valves and a micro surface tension piston. Each micro surface tension valve includes a gas channel and three liquid channels. The three liquid channels includes one middle liquid channel and two side liquid channels. One end of the gas channel is in communication with a gas. Another end of the gas channel communicates with one end of the middle liquid channel through a tapered microchannel. Two sides of the microchannel each are in communication with one end of each of the two side liquid channels through another tapered microchannel. Another end of the middle liquid channel and another end of one of the two side liquid channels are merged as a liquid inlet. Another end of the other of the two side liquid channels is as a liquid outlet. The micro surface tension piston includes a gas channel and a liquid channel. One end of the gas channel is in communication with a gas. Another end of the gas channel communicates with a middle section of the liquid channel through another tapered microchannel. One end of the liquid channel is connected with the liquid outlet of one of the two micro surface tension valves, and another end of the liquid channel is connected with the liquid inlet of the other of the two micro surface tension valves.

The mircrodevice of the present invention is controlled by the digital gas pressure of the microchannel inside the chip. Each microdevice uses the MISTA to separate the gas phase and the liquid phase, without any movable part and any special ventilating or elastic material. The pressure difference between the gas phase and the liquid phase is adapted to drive the gas-liquid interface, such that the microdevice can achieve the functions, such as sensing pressure, switching fluid channel, transporting liquid effectively, and so on. All kinds of microdevices can be shaped on the hard material (for example glass) by etching, so as to integrate a great lot microdevices with low cost, and the structure of chip and these several microdevices can be formed by adopting other methods on other material.

DETAILED DESCRIPTION OF THE PREFERRED EMBODIMENTS

Embodiments of the present invention will now be described, by way of example only, with reference to the accompanying drawings.

The present invention discloses a microdevice structure of a microchannel chip. The microdevice structure includes one gas channel and at least one liquid channel. The gas channel and each liquid channel are in communication with each other through a microchannel (capillary).

The theory of the present invention is that the gas-liquid interface in the microchannel has a certain relationship with the pressure difference between the gas phase and the liquid phase and the movement direction of the gas-liquid interface. This relationship can be used to achieve two objects, A: the movement of the gas-liquid interface can reflect the pressure difference between the gas phase and the liquid phase; B: the movement of the gas-liquid interface can be controlled by the pressure difference between the gas phase and the liquid phase.

The following embodiments are explained as examples.

Figure 1A:
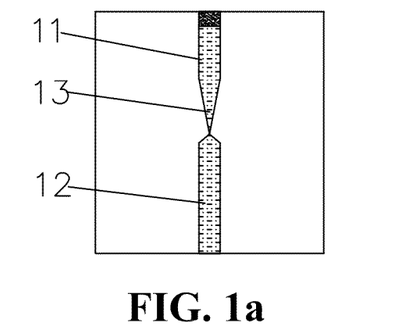
FIG. 1a, FIG. 1b and FIG. 1c are schematic views of a micro surface tension sensor.
Figure 1B:
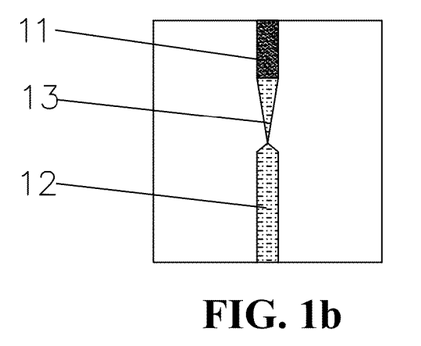
Figure 1C:
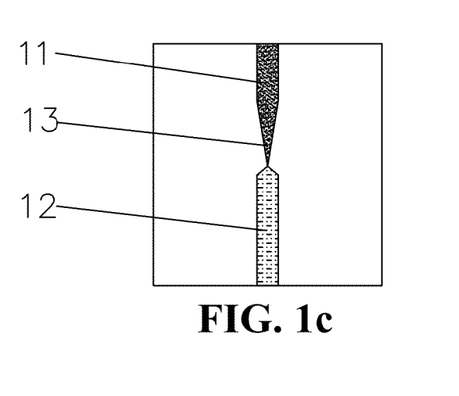

FIG. 1a, FIG. 1b and FIG. 1c are schematic views of a micro surface tension sensor. The micro surface tension sensor includes a gas channel 11 and a liquid channel 12 which are formed in a chip. One end of the gas channel 11 is in communication with a gas to receive gas pressure. Another end of the gas channel 11 communicates with one end of the liquid channel 12 through a tapered microchannel 13 (the narrow end of the microchannel 13 is an aperture). Another end of the liquid channel 12 is in communication with a liquid to receive liquid pressure.

The working principle of the MISEN (micro surface tension sensor) is that the middle of the microchannel 13 of the chip can accommodate the gas and the liquid. The interface tensions between the gas phase, the liquid phase and the solid phase are different to form the arc (commonly known as meniscus) of the gas-liquid interface. The surface tension of the gas-liquid interface, having a certain curvature, needs the pressure difference between the gas phase and the liquid phase to keep a balance, otherwise the interface will move. This effect is known as capillarity. The strength of the capillarity strengthens with decreasing the diameter of the capillary. For the microchannel 13 of the chip, the strength of the capillarity strengthens with decreasing the width of the microchannel 13 (equivalent to the diameter of the capillary). If the width of the microchannel 13 is gradually reduced like an elongate triangular shape, the gas-liquid interface located at different positions of the triangular microchannel 13 will have different strengths of capillarity relative to different pressure differences between the gas phase and the liquid phase. Thus, by the push of the pressure difference between the gas phase and the liquid phase, the location of the gas-liquid interface can be observed to show the pressure difference between the gas phase and the liquid phase. When the gas pressure is fixed and known, as shown in FIG. 1a, the liquid pressure is lowered to increase the pressure difference between the gas phase and the liquid phase so that the gas-liquid interface will move toward the liquid (referring to FIG. 1b). If the liquid pressure is continuously lowered, the gas-liquid interface will move to the apex of the triangle to communicate with the liquid channel, as shown in FIG. 1c. The apex is a MISTA (micro surface tension alveolus) to connect the MISEN (micro surface tension sensor) and the liquid channel. The gas-liquid interface in the MISTA has the maximum curvature or capillarity so the gas-liquid interface can be stopped here. Thus, the position of the gas-liquid interface shows the gas pressure. The triangular microchannel performs the assignment of the micro surface tension sensor. If the liquid pressure is fixed, the micro surface tension sensor can be used to measure the gas pressure.

Figure 2A:
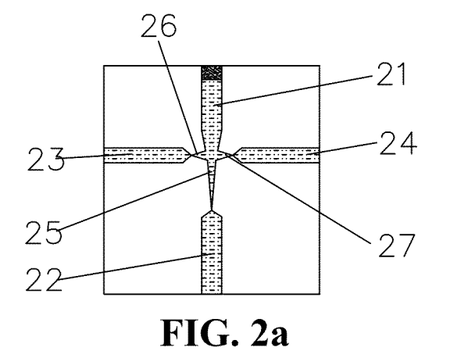
FIG. 2a, FIG. 2b and FIG. 2c are schematic views of a micro surface tension valve.
Figure 2B:
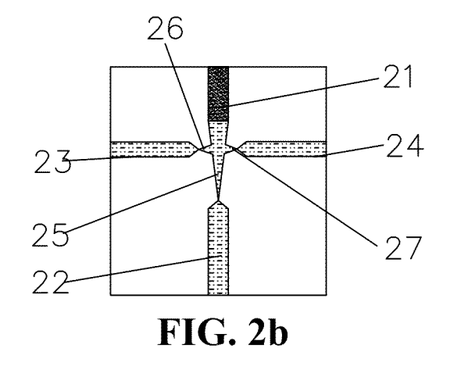
Figure 2C:
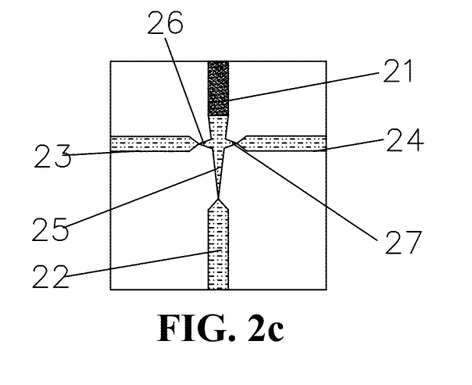

FIG. 2a, FIG. 2b and FIG. 2c are schematic views of a micro surface tension valve (MISVA). The micro surface tension valve includes a gas channel 21 and three liquid channels 22, 23, 24 which are formed in a chip. One end of the gas channel 21 is in communication with a gas. Another end of the gas channel 21 communicates with one end of the liquid channel 22 through a tapered microchannel 25. Two sides of the microchannel 25 are respectively in communication with one end of the liquid channel 23 through a tapered microchannel 26 (MISTA) to function as a liquid inlet and one end of the liquid channel 24 through a tapered microchannel 27 (MISTA) to function as a liquid outlet. The other ends of the three liquid channels 22, 23, 24 are respectively in communication with a liquid.

Because the greater pressure difference between the gas phase and the liquid phase inside the MISTA can form a stable gas-liquid interface which can stop the liquid or the gas from passing through the interface inside the MISTA. When the gas-liquid interface moves away from the MISTA, the liquid can pass through the MISTA. Two sides of the MISEN are respectively formed with a MISTA to communicate with two liquid channels. Referring to FIG. 2a, in general, the liquid channel at the top end is in communication with one side channel. When the gas pressure rises, the movement of the gas-liquid interface makes the MISEN filled with the gas (as shown in FIG. 2b and FIG. 2c) and the MISTAs at two sides form stable gas-liquid interfaces to stop the liquid channels from communicating with each other so as to cut off the liquid flow. This is equivalent to perform the shutting function of the MISVA. When the gas pressure is reduced, the gas-liquid interface will move back to the gas channel, such that the MISEN is filled with the liquid again and the liquid channels are in communication with each other again. This is equivalent to perform the opening function of the MISVA. Without any movable parts, the valve doesn't suffer wear and tear and has a long lifespan.

The micro surface tension valve may include a gas channel and two liquid channels. One end of the gas channel is in communication with a gas. Another end of the gas channel communicates with one end of one liquid channel through a tapered microchannel. Only one side (left or right) of the microchannel is further in communication with one end of the other liquid channel through a tapered microchannel (MISTA). The other ends of the two liquid channels are respectively in communication with a liquid.

Figure 5A:
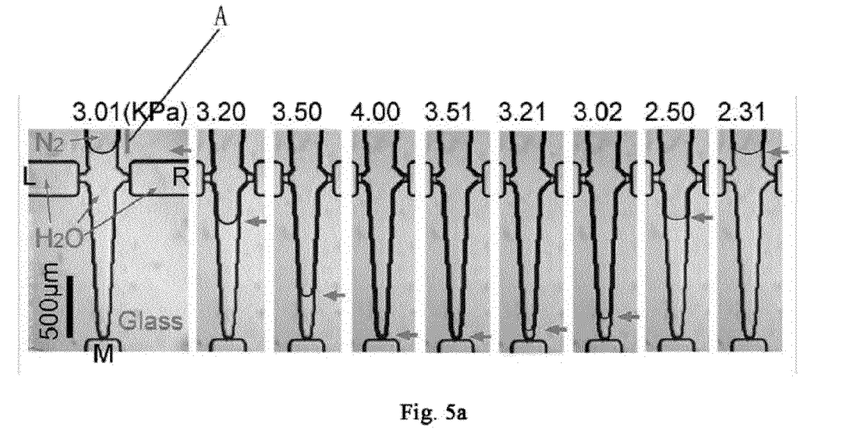
FIG. 5A shows the response of the gas-liquid interface in the MISVA to the gas pressure.
Figure 5B:
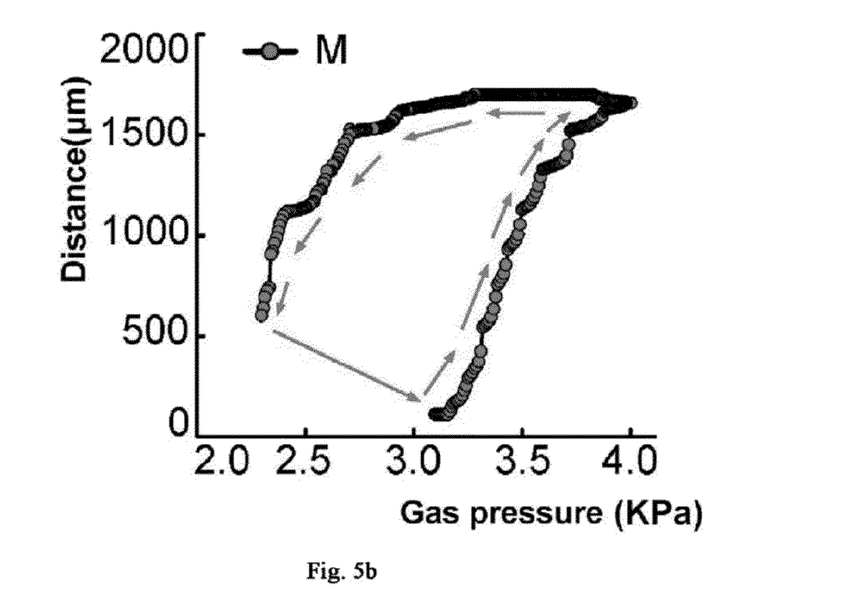
FIG. 5B shows the movement mode of the gas-liquid interface toward the M channel under different gas pressures.
Figure 5C:
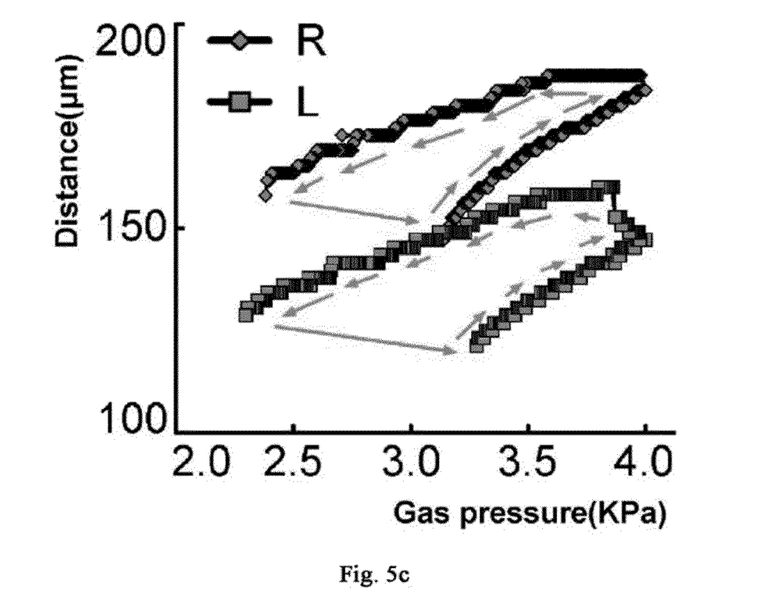
FIG. 5C shows the movement mode of the gas-liquid interface toward the left and right (L and R) channels under different gas pressures.
Figure 5D:
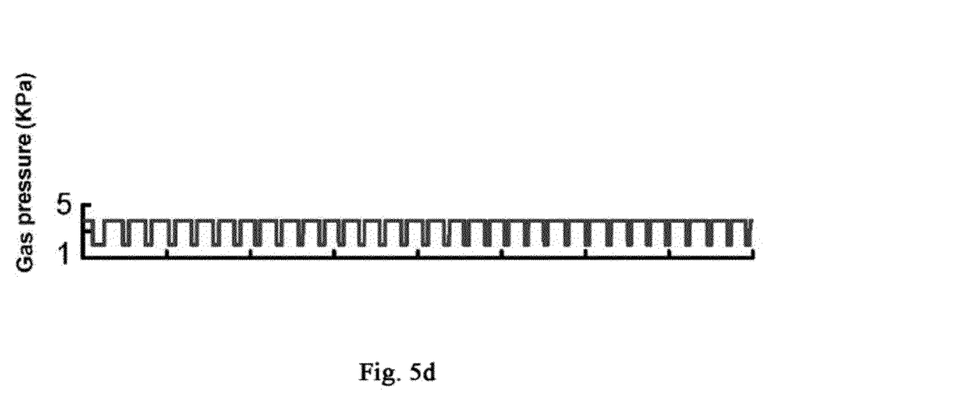
FIG. 5D is the digital gas pressure driving mode of the MISVA.
Figure 5E:
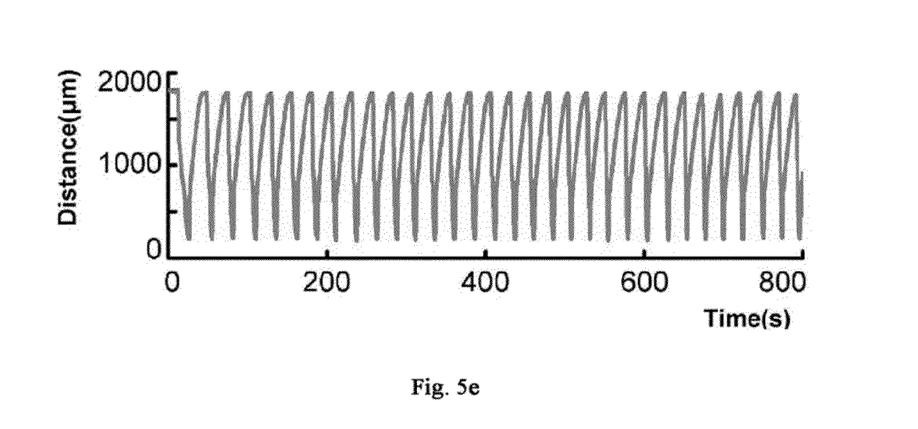
FIG. 5E is the response of the MISVA to the digital gas pressure driving.

FIG. 5A through FIG. 5E show the pressure difference between the gas phase and the liquid phase, the relationship of the position of the gas-liquid interface in the MISEN, and the reliable result after repeatedly testing. In detail, FIG. 5A shows the response of the gas-liquid interface to the gas pressure. In the V-shaped MISVA, the gas-liquid interface will move downward (toward the M channel) or move toward the L and R channels at left and right sides with the increase of the gas pressure (as shown in the upper portion of the drawing). The bold line A in the drawing is to show the measure way of the movement distance. FIG. 5B shows the movement mode of the gas-liquid interface toward the M channel under different gas pressures. The gas-liquid interface moves back and forth toward the M channel subject to the variation of the gas pressures. The movement distance is measured as shown in FIG. 5A and its direction is shown as the arrow. FIG. 5C shows the movement mode of the gas-liquid interface toward the left and right (L and R) channels under different gas pressures. The movement distance is measured as shown in FIG. 5A and its direction is shown as the corresponding arrow. FIG. 5D is the digital gas pressure driving mode of the MISVA. The gas pressure is set to 2 kPa and 4 kPa. The gas pressure is transformed repeatedly between the two gas pressures to drive the switch of the MISVA. FIG. 5E is the response of the MISVA to the digital gas pressure driving. The switching function of the MISVA is achieved by the movement of the gas-liquid interface. The periodic instruction of the digital gas pressure drives the gas-liquid interface to move regularly, reliably and precisely so as to achieve the switching function of the MISVA, namely, the function to switch on/off the microfluid.

Figure 6A:
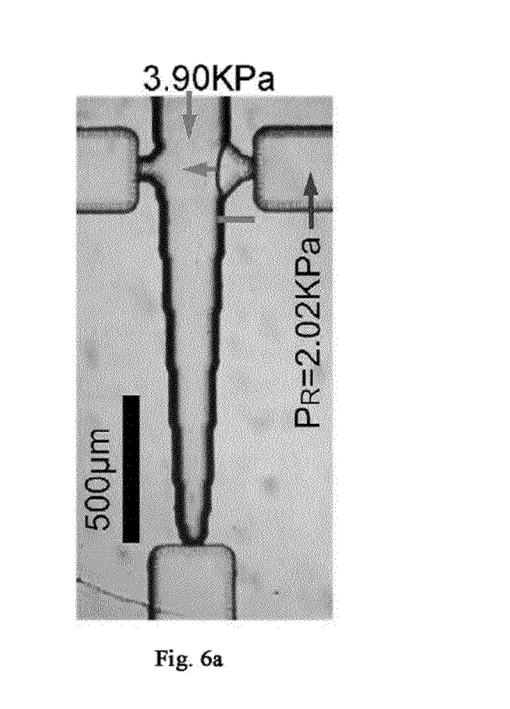
FIG. 6A is the leakage test of the MISVA under the pressure of the right channel.
Figure 6B:
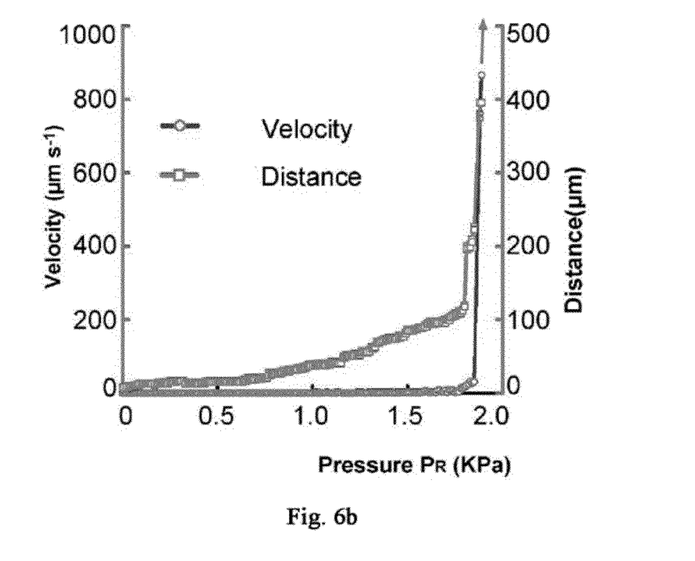
FIG. 6B shows the range of the MISVA to bear the reverse pressure from the right (R) channel.
Figure 6C:
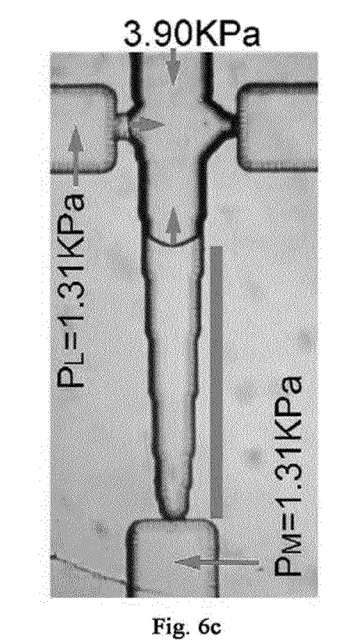
FIG. 6C is the leakage test of the MISVA under the pressures of the left (L) channel and the lower (M) channel.
Figure 6D:
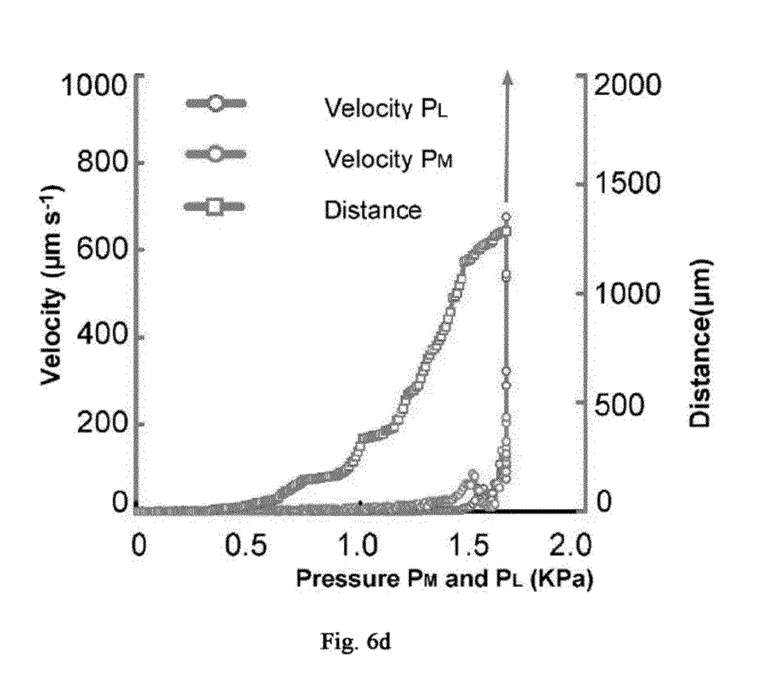
FIG. 6D shows the range of the MISVA to bear the reverse pressure from the left (L) channel and the lower (M) channel.

FIG. 6A through FIG. 6D are the test results of the functions of the MISVA. The data shows that the MISVA is able to bear 1.5 kPa pressure without leakage. In detail, FIG. 6A is the leakage test of the MISVA under the pressure of the right channel. Under a certain reverse pressure (from the right channel PR), the gas-liquid interface moves reversely. When the gas-liquid interface cannot bear the pressure to communicate with another channel, the MISVA will be leaking. FIG. 6B shows the range of the MISVA to bear the reverse pressure from the right (R) channel. When the pressure from the right channel increases, the gas-liquid interface will move under the pressure. When the pressure approaches 2 kPa, the movement of the gas-liquid interface exceeds the limitation to cause a leakage. The velocity of the leakage becomes high all at once. FIG. 6C is the leakage test of the MISVA under the pressures of the left (L) channel and the lower (M) channel. Under a certain reverse pressure (PL from the left channel L, and PM from the lower channel M), the gas-liquid interface moves reversely. When the gas-liquid interface cannot bear the pressure to communicate with another channel, the MISVA will be leaking. FIG. 6D shows the range of the MISVA to bear the reverse pressure from the left (L) channel and the lower (M) channel. When the pressure from the left channel increases, the gas-liquid interface will move under the pressure. When the pressure approaches 1.6-1.7 kPa, the movement of the gas-liquid interface exceeds the limitation to cause a leakage. The velocity of the leakage becomes high all at once.

Figure 3A:
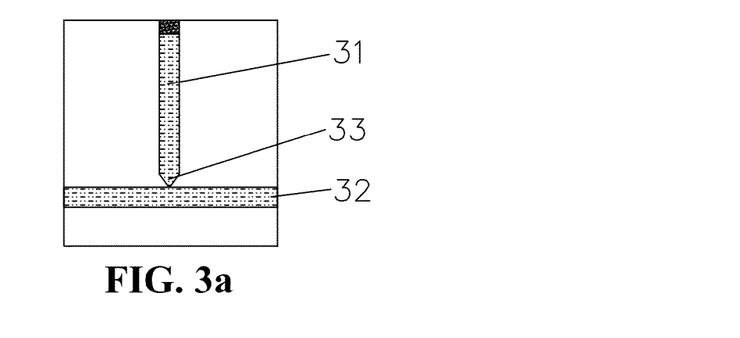
FIG. 3a, FIG. 3b and FIG. 3c are schematic views of a micro surface tension piston.
Figure 3B:
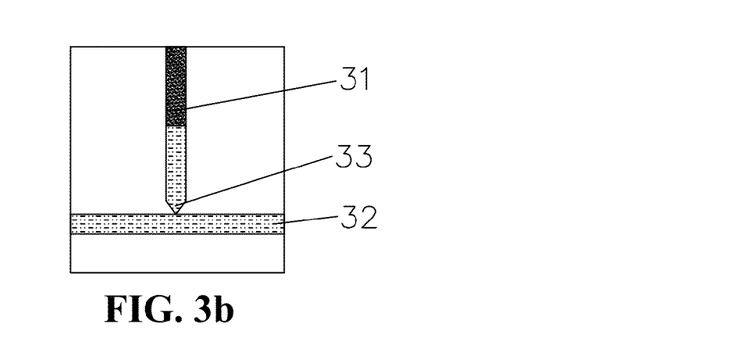
Figure 3C:
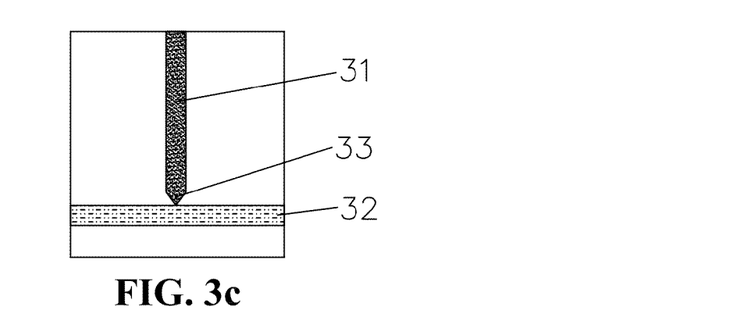

FIG. 3a, FIG. 3b and FIG. 3c are schematic views of a micro surface tension piston. The micro surface tension piston includes a gas channel 31 and a liquid channel 32 which are formed in a chip. One end of the gas channel 31 is in communication with a gas. Another end of the gas channel 31 communicates with a middle section of the liquid channel 32 through a tapered microchannel 33. Two ends of the liquid channel 32 are in communication with a liquid.

Like the working principle of the MISEN (micro surface tension sensor), the channel is designed to have an elongate and even width space to accommodate the movement of the gas-liquid interface with the MISTA to stop the gas from entering the liquid channel. This is a micro surface tension piston (MISTON). The volume of the MISTON can be limited through the length. When the gas pressure is low, the interface will move in the direction of the gas, and the liquid in the liquid channel will flow to the MISTON, as shown in FIG. 3a to FIG. 3c. When the gas pressure is high, the interface will move in the direction of the liquid, and the liquid in the MISTON will be poured into the liquid channel under the gas pressure.

The operation way of the MISTON is similar to the MISEN.

Figure 4A:
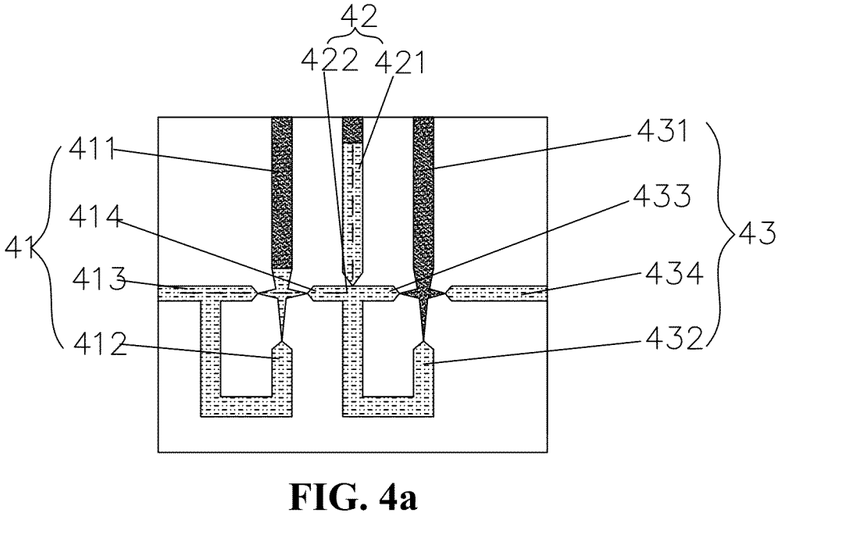
FIG. 4a and FIG. 4b are schematic views of a micro surface tension pump.
Figure 4B:
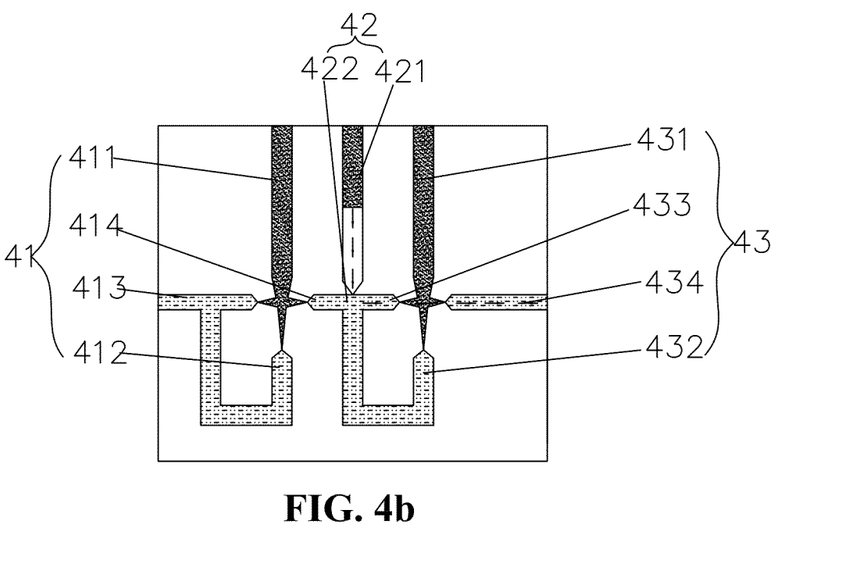

FIG. 4a and FIG. 4b are schematic views of a MISPU (micro surface tension pump). The MISPU is as a power microdevice composed of two MISVAs 41, 43 and a MISTON 42. The MISVA 41 includes a gas channel 411 and three liquid channels 412, 413, 414. The MISVA 43 includes a gas channel 431 and three liquid channels 432, 433, 434. The structure of the MISVAs 41, 43 is the same as the aforesaid. The other end of the liquid channel 412 of the MISVA 41 and the other end of the liquid channel 413 are merged as a liquid inlet of the MISVA 41. The other end of the liquid channel 414 is as a liquid outlet of the MISVA 41. The other end of the liquid channel 432 of the MISVA 43 and the other end of the liquid channel 433 are merged as a liquid inlet of the MISVA 43. The other end of the liquid channel 434 is as a liquid outlet of the MISVA 43. The MISTON 42 includes a gas channel 421 and a liquid channel 422. The structure of the MISTON 42 is the same as the aforesaid. In the MISPU, one end of the liquid channel 422 is connected with the liquid outlet of the MISVA 41, and the other end of the liquid channel 422 is connected with the liquid inlet of the MISVA 43.

The MISVA 41 is as an inlet valve and the MISVA 43 is as an outlet valve (both exchangeable). The MISTON 42 is as an inhaler and injector. By using a series of digital gas pressure control, a stable pump output is derived. When the inlet valve is opened as shown in FIG. 4a, the outlet valve is closed and the MISTON 42 inhales the liquid from the inlet valve. When the MISTON 42 is filled with the liquid, the inlet valve is closed and the outlet valve is opened as shown in FIG. 4b to release the liquid in the MISTON 42 through the outlet valve. Thus, the working loop of the MISPU is closed. Continuous loop, the liquid is continuously inhaled from the inlet valve and injected into the next microchannel through the outlet valve so as to form a pump output.

Figure 7A:
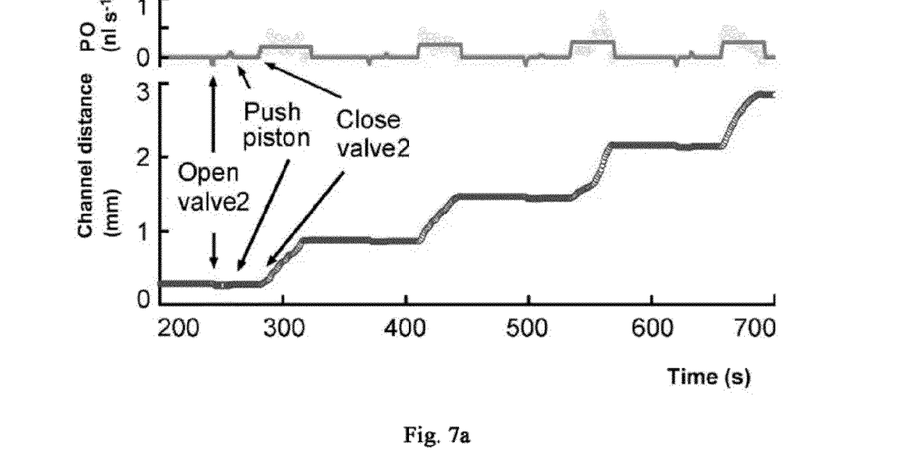
FIG. 7A is a power test showing the MISPU to push the bubble.
Figure 7B:
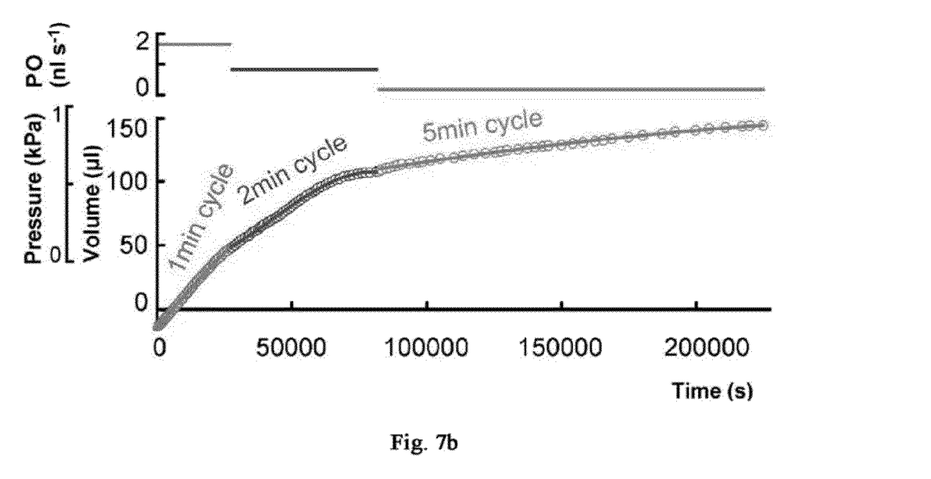
FIG. 7B shows the output power of the MISPU in different circles.
Figure 7C:
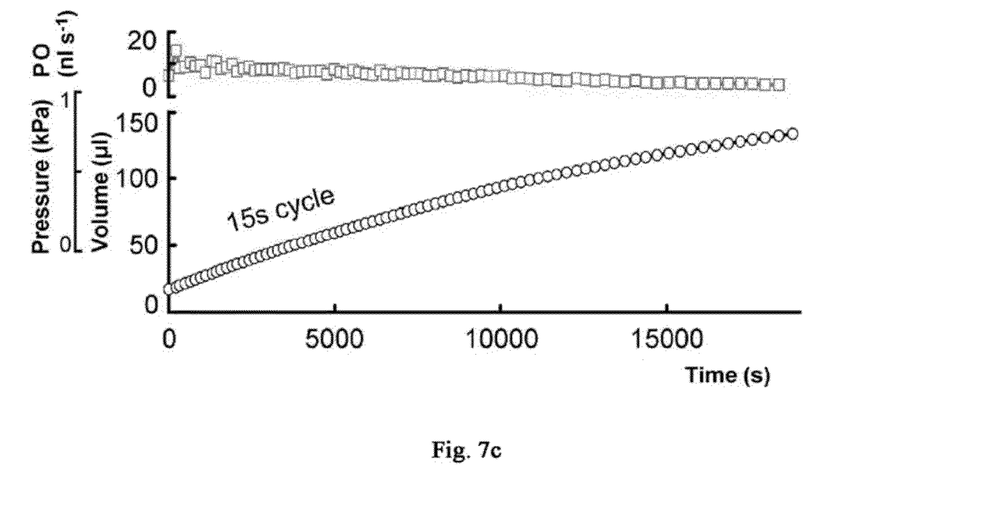
FIG. 7C shows the change of the shortest pump circle and the largest pump output under the reverse pressure.
Figure 7D:
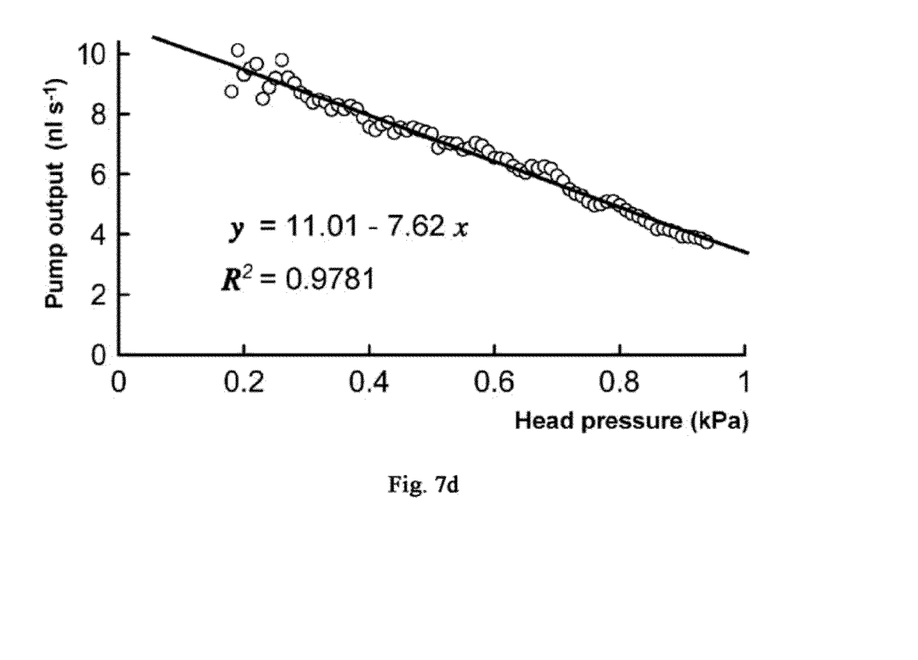
FIG. 7D shows the relationship between the head pressure and the pump output.

FIG. 7A, FIG. 7B and FIG. 7C are the test results of the pump output. The fastest pump output can reach 10 nl/s. In detail, FIG. 7A is a power test showing the MISPU to push the bubble. The MISPU is used to push the bubble in the channel. The power of the MISPU during each process is calculated by measuring the movement of the bubble in the microchannel. In the drawing, PO is the pump output derived by calculating. The drawing shows the pump output data when the MISVA and the MISTON are operated. FIG. 7B shows the output power of the MISPU in different circles. In the drawing, different line segments and digits show the volume output data of different pump circles. The reverse pressure applied to the front end of the MISPU is also shown in the drawing. Because the volume of the pump output direct enters the vertical channel, the volume of the pump output can be translated into the reverse pressure (kPa). FIG. 7C shows the change of the shortest pump circle and the largest pump output under the reverse pressure. The MISPU is set to be the fastest (the pump circle is 15 s). When the reverse pressure is increased continuously, the output capacity of the MISPU gradually weakens (the upper line). FIG. 7D shows the relationship between the head pressure and the pump output. When the head pressure increases (derived by the measure of the reverse pressure), the pump output is lowered.

Figure 8:
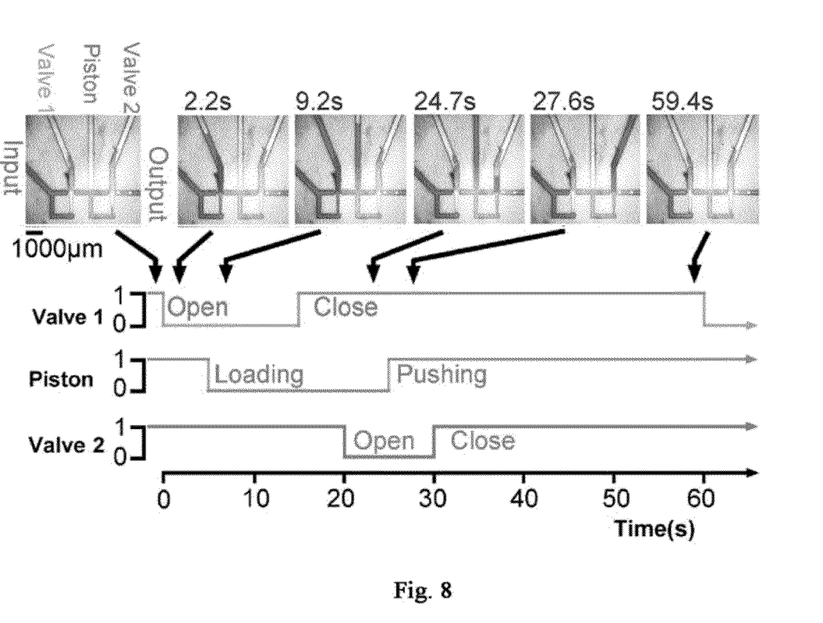
FIG. 8 is a schematic view showing that the operation mode of the MISPU is controlled by the digital gas pressure.

FIG. 8 is a schematic view showing that the operation mode of the MISPU is controlled by the digital gas pressure. The gas pressure is simply set to a high pressure and a lower pressure, namely, 0 and 1. Through the digital gas pressure instruction sent to the inlet valve, the MISTON and the outlet valve, the MISPU starts to work so as to bring a certain head pressure and flow. In the drawing, different line segments show the working situations of different pumps under the drive of the digital gas pressure instruction.

The mircrodevice of the present invention is controlled by the digital gas pressure of the microchannel inside the chip. Each microdevice uses the MISTA to separate the gas phase and the liquid phase, without any movable part and any special ventilating or elastic material. The pressure difference between the gas phase and the liquid phase is adapted to drive the gas-liquid interface, such that the microdevice can achieve the functions, such as sensing pressure, switching fluid channel, transporting liquid effectively, and so on.

The control way of the aforesaid microdevice is similar to the digital circuit control. Two fixed high and low gas pressure are set, the control system uses the pressure difference between the gas phase and the liquid phase to achieve the automatic control of the microdevice. This is an easy, reliable and simply microchannel control device.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A microdevice structure of a microchannel chip, including a gas channel and at least one liquid channel, the gas channel communicating with the at least one liquid channel through a microchannel, wherein the microdevice structure is a micro surface tension valve, the micro surface tension valve including a gas channel and three liquid channels, one end of the gas channel being in communication with a gas, another end of the gas channel communicating with one end of one of the three liquid channels through a tapered microchannel, two sides of the microchannel being respectively in communication with one end of each of the other two liquid channels through another tapered microchannel, another end of each of the three liquid channels being in communication with a liquid.

2. A microdevice structure of a microchannel chip, including a gas channel and at least one liquid channel, the gas channel communicating with the at least one liquid channel through a microchannel, wherein the microdevice structure is a micro surface tension pump composed of two micro surface tension valves and a micro surface tension piston, each micro surface tension valve including a gas channel and three liquid channels, the three liquid channels including one middle liquid channel and two side liquid channels, one end of the gas channel being in communication with a gas, another end of the gas channel communicating with one end of the middle liquid channel through a tapered microchannel, two sides of the microchannel each being in communication with one end of each of the two side liquid channels through another tapered microchannel, another end of the middle liquid channel and another end of one of the two side liquid channels being merged as a liquid inlet, another end of the other of the two side liquid channels being as a liquid outlet; the micro surface tension piston including a gas channel and a liquid channel, one end of the gas channel being in communication with a gas, another end of the gas channel communicating with a middle section of the liquid channel through another tapered microchannel, one end of the liquid channel being connected with the liquid outlet of one of the two micro surface tension valves, and another end of the liquid channel being connected with the liquid inlet of the other of the two micro surface tension valves.

* * * * *